United States Patent
Silvis et al.

(10) Patent No.: US 6,823,748 B2
(45) Date of Patent: Nov. 30, 2004

(54) ACTIVE PULSATION CANCELLATION DEVICE FOR DIESEL PARTICULATE SAMPLING SYSTEMS

(75) Inventors: William Martin Silvis, Ann Arbor, MI (US); Norbert Kreft, Ann Arbor, MI (US); Wolfgang Schindler, Graz (AT); Gerald Marek, Ann Arbor, MI (US)

(73) Assignee: AVL North America Inc., Plymouth, MI (US)

( * ) Notice: Subject to any disclaimer, the term of this patent is extended or adjusted under 35 U.S.C. 154(b) by 101 days.

(21) Appl. No.: 10/122,154

(22) Filed: Apr. 12, 2002

(65) Prior Publication Data

US 2002/0157482 A1 Oct. 31, 2002

Related U.S. Application Data

(60) Provisional application No. 60/283,877, filed on Apr. 13, 2001.

(51) Int. Cl.[7] .................................................. G01N 1/00
(52) U.S. Cl. ...................................................... 73/863.03
(58) Field of Search ............................ 73/23.31, 23.32, 73/23.33, 863.01, 863.02, 863.03, 863.58, 864.73, 864.81

(56) References Cited

U.S. PATENT DOCUMENTS

| 5,052,425 | A |   | 10/1991 | Hohenberg et al. |          |
|-----------|---|---|---------|------------------|----------|
| 5,337,595 | A | * | 8/1994  | Lewis            | 73/23.31 |
| 5,469,731 | A | * | 11/1995 | Decker et al.    | 73/23.31 |
| 6,062,092 | A | * | 5/2000  | Weaver           | 73/863.03 |
| 6,200,819 | B1 |  | 3/2001  | Harvey et al.    |          |

FOREIGN PATENT DOCUMENTS

| EP | 0611962 A1 | 8/1994  |
|----|------------|---------|
| JP | 59201915   | 11/1984 |

OTHER PUBLICATIONS

Search Report EP02450084.

* cited by examiner

Primary Examiner—Robert Raevis
(74) Attorney, Agent, or Firm—Carlson, Gaskey & Olds

(57) ABSTRACT

A particulate sampler is provided for conveying exhaust gas from exhaust gas source to analysis equipment. The particulate sampler includes a probe for receiving the exhaust gas and a transfer tube for conveying the exhaust gas from a tailpipe to a mixer. The mixer mixes the exhaust gas and a dilution gas from a dilution source. A dilution tunnel mixes and conveys the exhaust gas and dilution gas from the mixer to analysis equipment such as a filter or gas analyzers. A flow pulsation cancellation device includes an actuator in communication with at least one of the tailpipe, probe, transfer tube, mixer, and dilution tunnel for introducing a canceling pressure pulse to minimize the effects of pressures pulses present from the tailpipe within the sampler. The actuator may be a moveable membrane or a fluid flow control valve. Pressure sensors are used to measure the pressure of the undiluted and diluted exhaust gas, and a controller determines the desired canceling pressure pulse based upon the measured pressures.

5 Claims, 2 Drawing Sheets

ACTIVE PULSATION CANCELLATION DEVICE FOR DIESEL PARTICULATE SAMPLING SYSTEMS

REFERENCE TO RELATED APPLICATIONS

This application claims priority to U.S. Provisional Patent Application No. 60/283,877, filed on Apr. 13, 2001.

BACKGROUND OF THE INVENTION

The invention relates to an exhaust gas sampling system, and more particularly, the invention relates to a diesel particulate sampling system.

Diesel circulate sampling systems are used to measure particulate matter in the diesel exhaust gas. Raw exhaust is collected from the tailpipe with a probe arranged with the tailpipe. The raw exhaust gas is typically diluted with a dilution gas, homogeneously mixed, and collected by a filter for subsequent measurement. A constant dilution ratio must be maintained so that the quantity of exhaust gas is known when measuring the particulate matter to accurately determine the particulate matter concentration in the exhaust gas.

It may be desirable to utilize a shorter probe for a diesel particulate sampler to provide more accurate detection and measurement of particular matter. Utilizing a significantly shorter probe than the prior art may cause the sampler to be more sensitive to flow and pressure fluctuations present in the tailpipe. Internal combustion engines cause cyclic exhaust fluctuations as the engine pistons reciprocate and exhaust valves open. During a pressure drop, sample exhaust gas and dilution gas may be undesirably drawn out of the probe and back into the tailpipe, thereby changing the dilution ratio in an uncontrolled manner. The portion of the probe with the tailpipe may be lengthened to minimize the effects of the pressure fluctuations. However, the remaining effects of the pressure fluctuations may be undesirable in that the changes in dilution ratio are still unacceptable. As a result, it may be desirable to actively apply pressure pulses within the sampler to cancel pressure pulses from the tailpipe in order to use shorter probes.

SUMMARY OF THE INVENTION AND ADVANTAGES

The present invention provides a particulate sampler for conveying exhaust gas from exhaust gas source to analysis equipment. The particulate sampler includes a probe for receiving the exhaust gas and a transfer tube for conveying the exhaust gas from a tailpipe to a mixer. The mixer mixes the exhaust gas and a dilution gas from a dilution source. A dilution tunnel mixes and conveys the exhaust gas and dilution gas from the mixer to analysis equipment such as a filter or gas analyzers. A flow pulsation cancellation device includes an actuator in communication with at least one of the tailpipe, probe, transfer tube, mixer, and dilution tunnel for introducing a canceling pressure pulse to minimize the effects of pressures pulses present from the tailpipe within the sampler. The actuator may be a moveable membrane or a fluid flow control valve. Pressure sensors are used to measure the pressure of the undiluted and diluted exhaust gas, and a controller determines the desired canceling pressure pulse based upon the measured pressures.

Accordingly, the above invention provides a device that actively applies pressure pulses within the sampler of a nature sufficient to cancel the pressure pulses from the tailpipe

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENT

Figure 1A:
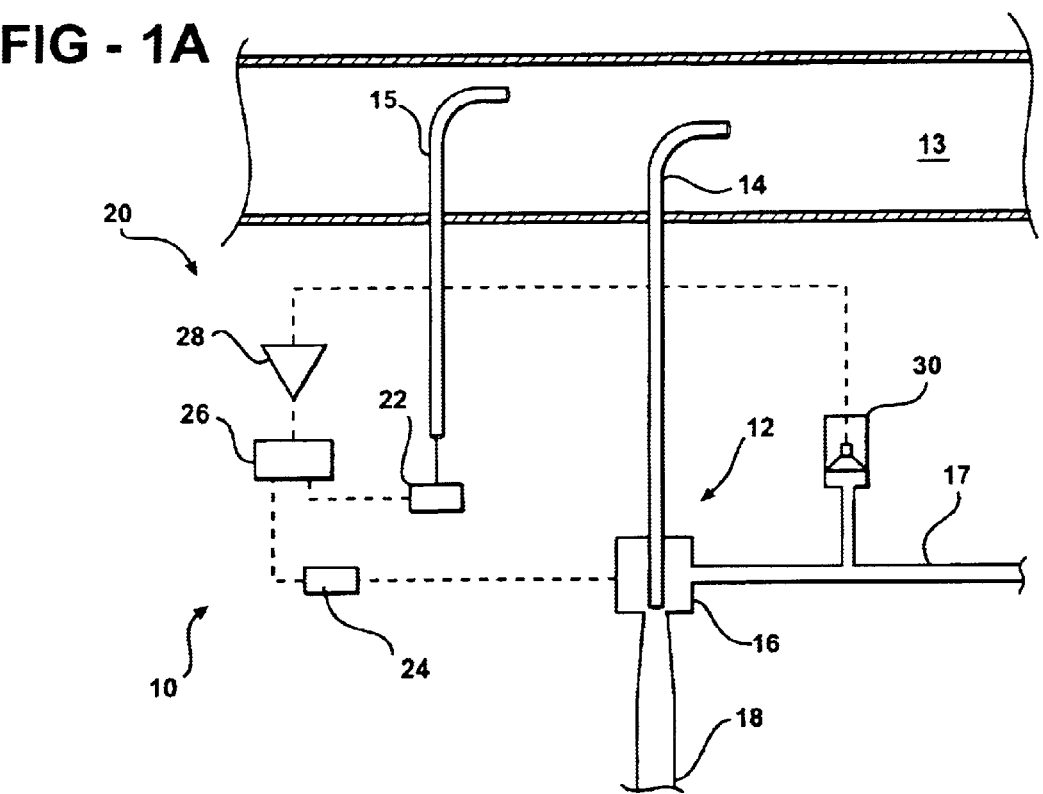
FIG. 1a is a schematic view of one embodiment of a pulsation cancellation device utilizing a membrane.
Figure 1B:
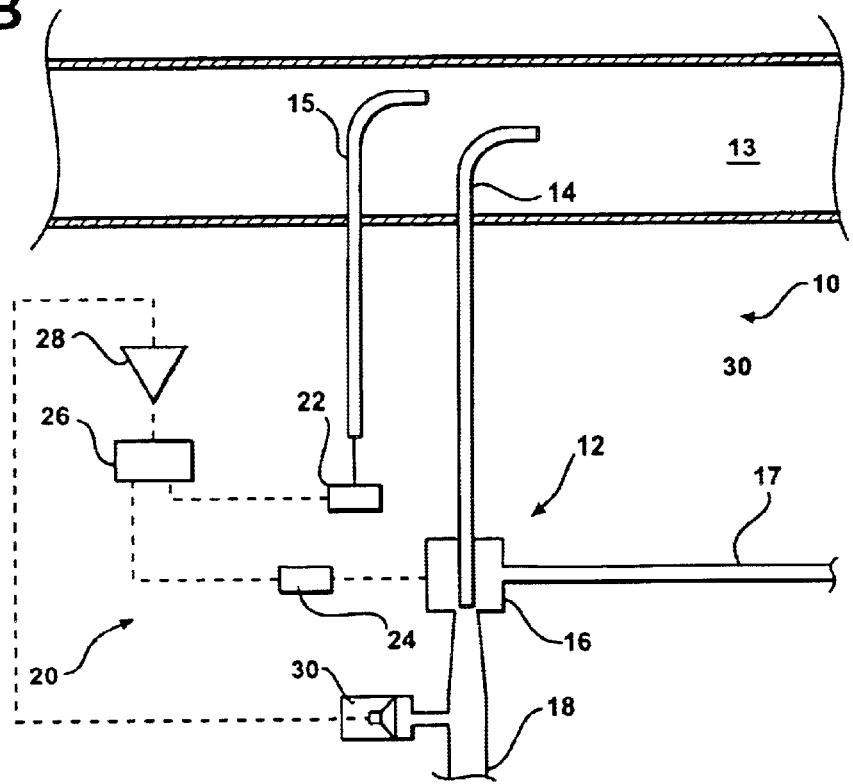
FIG. 1b is a schematic view of another embodiment of the pulsation cancellation device utilizing a membrane.
Figure 2:
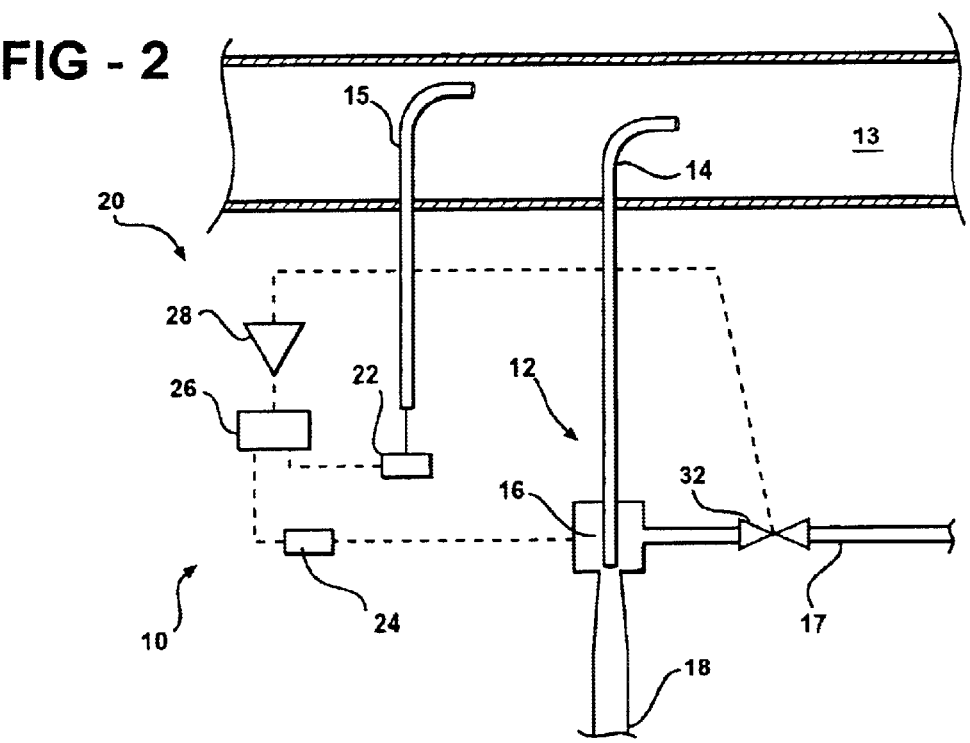
FIG. 2 is a schematic view of yet another embodiment of the pulsation cancellation device utilizing a proportional control valve.

A particulate sampler 10, which is shown in FIGS. 1a, 1b and 2, is used in the collection and measurement of particulate matter in diesel engine exhaust. The particulate sampler 10 preferably includes multiple components that are removably secured to one another. The components are typically constructed from stainless steel, which withstands the harsh environment of the vehicle exhaust gases. While the present invention is disclosed in terms of a diesel particulate sampler, it is to be understood that the invention may be applied to other exhaust gas samplers.

The sampler 10 includes a transfer tube assembly 12 having a probe 14. The probe 14 typically includes a curved or straight end portion that is arranged in a tailpipe 13. The probe 14 collects a small exhaust gas sample that contains particulate matter. The probe 14 conveys the exhaust gas sample to a mixer 16 where a dilution gas, which is of a type know in the art, is introduced to the exhaust gases. Passageway 17 carries the dilution gas from the dilution gas source to the mixer 16. The dilution and exhaust gases are conveyed through a tunnel 18 where they are homogeneously mixed together. A filter may be connected to the end of the tunnel 18 for collecting the particulate matter on a filter or other similar device. Alternatively, an analyzer may be connected to the end of the tunnel 18 for analysis of the exhaust gas sample.

FIGS. 1a and 1b depict the present invention pulsation cancellation device utilizing a membrane, or speaker-like device, driven by an actuator. As shown in FIG. 1a, a pressure cancellation system 20 includes a pressure sensor, such as the pressure sensor indicated at 22, for sensing the pressure fluctuations within the tailpipe 13. The pressure sensor 22 is in communication with the tailpipe 13 through tube 15. Alternatively, the pressure may be measured at the inlet of the probe 14 to eliminate the need for a separate tube 15. The pressure within the particulate sampler 10 may be measured at a location such as the tunnel 18 or at the mixer 16 (shown in FIGS. 1a and 1b). Alternatively, the pressure may be measured at the end of the transfer tube 12 inside the mixer 16. It is to be understood that the pressure sensors may be located at any suitable location within the sampler 10 to measure the pressure of the exhaust gas from the tailpipe and the pressure of exhaust and dilution gases within the sampler 10.

A controller 26 is connected to the pressure sensors 22 and 24 for canceling the effects of the pressure pulses from the tailpipe 13 on the sampler 10. The controller 26 commands an amplifier 28 to drive an actuator 30 such as a membrane or other similar device to introduce a pressure wave within a fluid passageway associated with the tunnel 18 or mixer 16. For example, as shown in FIG. 1a, the actuator 30 may be in communication with the passageway 17. Alternatively, the actuator 30 may be in communication with the dilution tunnel 18, as shown in FIG. 1b. It is to be understood that the actuator 30 may be situated along any portion of a passageway within the sampler 10 in any suitable position, which is best determined through testing of the system.

In operation, an exhaust pressure pulse is detected by pressure sensor 22. The controller 26 then calculates the electric energy needed to create a pressure pulse within the sampler 10 of sufficient magnitude and in phase with the pressure pulse detected by sensor 22. The controller 26 commands the amplifier 28 to drive the actuator to introduce a pressure pulse within the sampler 10 to cancel the effects of the pressure pulse from the tailpipe 13. The amplitude and phase of the pressure cancellation pulse produced by the actuator 30 is of a sufficient nature to significantly prevent undesirable changes in the flow rate of sampled gases in the probe 12 and transfer tube 14. Closed loop feedback for the controller is used to gauge the effectiveness of the control. Feedback is provided from pressure transducer 24, whose reading ideally differs from the reading from pressure transducer 22 by a stable amount consistent with the desired flow in the probe 14 and transfer tube 12.

Alternatively, the undesirable pressure wave introduced by the tailpipe 13 may be cancelled utilizing a proportional control valve 32. The proportional control valve 32 varies the dilution gas flow rate introduced into the mixer 16. The flow of dilution gas may be increased or decreased to cancel the effects of the pressure pulse introduced by the tailpipe 13. Changes in the amount of flow fill and empty the volume internal to the sampling system, changing its internal pressure in the desired manner. The control of the proportional control valve 32 is similar to that of the actuator 30, described in relation to FIGS. 1a and 1b above.

Figure 3:
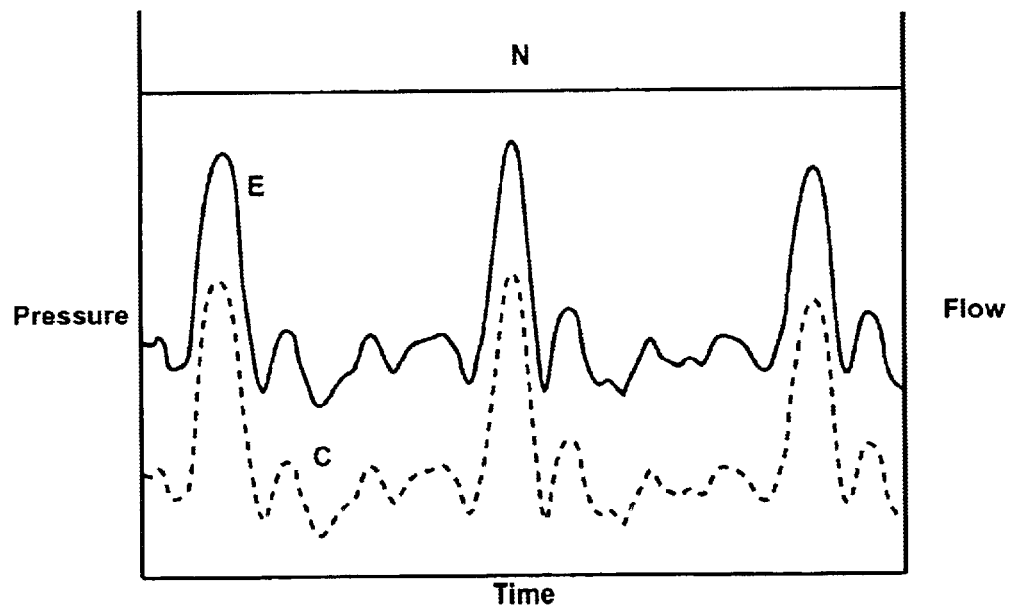
FIG. 3 is a graphical view of pulsation cancellation utilizing the present invention.

The pressure pulse cancellation is graphically depicted in FIG. 3. An undesired pressure pulse E is introduced by the tailpipe 13. A pressure pulse C is introduced by the system 20 in phase with the pressure pulse from the tailpipe 13. The pulse C is produced in response to the measured pulse E to cancel the pulse E and maintain a constant pressure difference and consequent flow of gases through the sampler 10, as depicted by curve N. The constant pressure curve N enables accurate control of the dilution ratio. In this manner, the flow pulsation cancellation device 20 keeps the differential pressure over the length of the probe 14 and transfer tube 12 free of fluctuations and therefore greatly minimizes or eliminates the negative effects of the undesirable pressure pulses introduced by the tailpipe 13.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

What is claimed is:

1. A particulate sampler for conveying exhaust gas from exhaust gas source to analysis equipment, said particulate sampler comprising:

a probe for receiving undiluted exhaust gas;

a mixer in fluid communication with the probe and mixing the exhaust gas and a dilution gas;

a dilution tunnel for mixing and conveying the exhaust gas and dilution gas from said mixer to analysis equipment;

a flow pulsation cancellation device having an actuator in communication with a transfer tube assembly that includes the probe, the mixer, and the dilution tunnel for introducing a canceling pressure pulse to minimize the effects of pressures pulses present from the exhaust gas source within the sampler; and wherein said flow pulsation cancellation device includes a controller connected to first and second pressure sensors respectively in communication with undiluted and diluted exhaust gas, said controller determining a pressure differential between said sensors and producing said canceling pressure pulse in response to said pressure differential.

2. The sampler according to claim 1, wherein said flow pulsation cancellation device includes an amplifier arranged between said controller and said actuator amplifying a signal from said controller to said actuator.

3. A sampler for conveying exhaust gas from exhaust gas source to analysis equipment, said sampler comprising:

a probe for receiving undiluted exhaust gas;

a mixing assembly mixing the exhaust gas and a dilution gas;

a flow pulsation cancellation device having an actuator in communication with a transfer tube assembly that includes the probe and the mixing assembly for introducing a canceling pressure pulse to minimize the effects of pressures pulses from the exhaust gas source within the sampler; and wherein said flow pulsation cancellation device includes a controller connected to first and second pressure sensors respectively in communication with undiluted and diluted exhaust gas, said controller determining a pressure differential between said sensors and producing said canceling pressure pulse in response to said pressure differential.

4. The sampler according to claim 3, wherein said flow pulsation cancellation device includes an amplifier arranged between said controller and said actuator amplifying a signal from said controller to said actuator.

5. A method of canceling pressure pulses from a tailpipe in an exhaust gas sampler comprising the steps of:

a) sensing a first pressure of an undiluted exhaust gas indicative of an undesired exhaust gas pressure fluctuation;

b) sensing a second pressure of a diluted exhaust gas;

c) determining a desired canceling pressure pulse from the first and second pressures; and d) producing the desired canceling pressure pulse in the sampler.

* * * * *